(12) United States Patent
Ruch

(10) Patent No.: US 11,992,721 B2
(45) Date of Patent: May 28, 2024

(54) FLAME ARRESTER FOR PROCESS DEVICES

(71) Applicant: Rosemount Inc., Shakopee, MN (US)

(72) Inventor: Tyrel L. Ruch, Saint Paul, MN (US)

(73) Assignee: Rosemount Inc., Shakopee, MN (US)

(*) Notice: Subject to any disclaimer, the term of this patent is extended or adjusted under 35 U.S.C. 154(b) by 834 days.

(21) Appl. No.: 16/923,532

(22) Filed: Jul. 8, 2020

(65) Prior Publication Data

US 2022/0008770 A1    Jan. 13, 2022

(51) Int. Cl.
*A62C 4/02* (2006.01)
*A62C 4/04* (2006.01)
*B22F 10/00* (2021.01)
*F23D 14/72* (2006.01)
*F23N 5/00* (2006.01)
*G01N 33/00* (2006.01)

(52) U.S. Cl.
CPC .............. *A62C 4/02* (2013.01); *A62C 4/04* (2013.01); *B22F 10/00* (2021.01); *F23D 14/72* (2013.01); *F23N 5/006* (2013.01); *G01N 33/0009* (2013.01); *B22F 2301/052* (2013.01); *B22F 2301/15* (2013.01); *B22F 2301/35* (2013.01)

(58) Field of Classification Search
CPC ..... G01N 33/0009; F23N 5/006; F23D 14/72; A62C 4/02
USPC ......................................................... 431/346
See application file for complete search history.

(56) References Cited

U.S. PATENT DOCUMENTS

| 5,203,295 A | 4/1993 | Alexander |
| 8,485,040 B2 | 7/2013 | Petersen |
| 2010/0311001 A1 | 12/2010 | Helmsen et al. |
| 2011/0108292 A1* | 5/2011 | Moyer ................. A62C 4/00 169/48 |
| 2012/0234097 A1 | 9/2012 | Petersen |
| 2016/0305653 A1* | 10/2016 | Fields ................ F23D 14/825 |
| 2017/0003246 A1 | 1/2017 | Shuk et al. |
| 2018/0056100 A1 | 3/2018 | Cockerham et al. |
| 2018/0056101 A1 | 3/2018 | Cockerham et al. |

FOREIGN PATENT DOCUMENTS

| CN | 110575635 A | 12/2019 |
| WO | 2016103386 A1 | 6/2016 |

OTHER PUBLICATIONS

ZGF2 Series Zirconia Oxygen Probe (https://library.e.abb.com/public/75a9fcf67fbb066ec125781500479637/DS_ZFG2-EN_L.pdf).*

(Continued)

*Primary Examiner* — Vivek K Shirsat
(74) *Attorney, Agent, or Firm* — Christopher R. Christenson; Kelly, Holt & Christenson, P.L.L.C.

(57) ABSTRACT

A flame arrester for a process device is provided. The flame arrester includes a flame arrester element formed of a first helix having a first axis and a second helix having a second axis, wherein the first axis and the second axis are unparallel. A housing configured to mount to the process device. The flame arrester element is mounted to the housing. A combustion analyzer employing an improved flame arrester is provided along with a method of manufacturing an improved flame arrester for process devices.

16 Claims, 12 Drawing Sheets

(56) References Cited

OTHER PUBLICATIONS

"Emerson Combustion Analysis Solutions Improve Boiler Efficiency and Uptime" retrieved from https://www.emerson.com/documents/automation/flyer-combustion-analysis-solutions-rosemount-en-70334.pdf, Emerson 2017, 10 pages.
International Search Report Written Opinion, dated Oct. 8, 2021, for International Patent Application No. PCT/US2021/037600, 8 pages.
First Office Action for Japanese Patent Application No. 2023-501019, dated Jan. 9, 2024, 9 pages including English Translation.

* cited by examiner

FLAME ARRESTER FOR PROCESS DEVICES

BACKGROUND

Process devices use flame arresters to ensure that flammable vapors are not ignited by potential sources of ignition, such as flares, exothermic chemical reactions, flames, and/or high temperature surfaces. Flame arresters can be used in a variety of process applications including, without limitation, chemical plants, refining operations, petrochemical applications, biogas applications, landfills, et cetera. A flame arrester is typically installed in a location or device between a source of fuel and an ignition source and includes one or more flow paths through the flame arrester that are designed to allow gas flow therethrough, but also to remove heat from the flame front as the flame front attempts to flow through the path(s). In this way, a flame arrester prevents a flame front from reaching a fuel source thus preventing ignition of the fuel source, and also preventing damage to property and injury to personnel.

One particular application for flame arresters is in combustion analyzers. Combustion analyzers provide a measurement of the oxygen remaining in the flue gases coming from any combustion process. By maintaining the ideal level of oxygen, optimal efficiency is gained and the lowest levels of $NO_x$, CO, and $CO_2$ are produced. This facilitates compliance with environmental regulations. One example of a commercially-available combustion analyzer is sold under the trade designation Model 6888 In Situ Flue Gas Oxygen Transmitter by Rosemount Inc., an Emerson Automation Solutions company.

In a combustion analyzer, a flame arrester is used in the combustion probe to allow the hot gasses to flow through to the oxygen sensing cell for gas measurements. These gasses are generally hot enough to generate a source of ignition and so the flame arrester is used to reduce the temperature of the gasses and to minimize the amount of oxygen around the gasses thereby minimizing the risk of ignition or explosion.

SUMMARY

A flame arrester for a process device is provided. The flame arrester includes a flame arrester element formed of a first helix having a first axis and a second helix having a second axis, wherein the first axis and the second axis are unparallel. A housing configured to mount to the process device. The flame arrester element is mounted to the housing. A combustion analyzer employing an improved flame arrester is provided along with a method of manufacturing an improved flame arrester for process devices.

DETAILED DESCRIPTION OF ILLUSTRATIVE EMBODIMENTS

Figure 1:
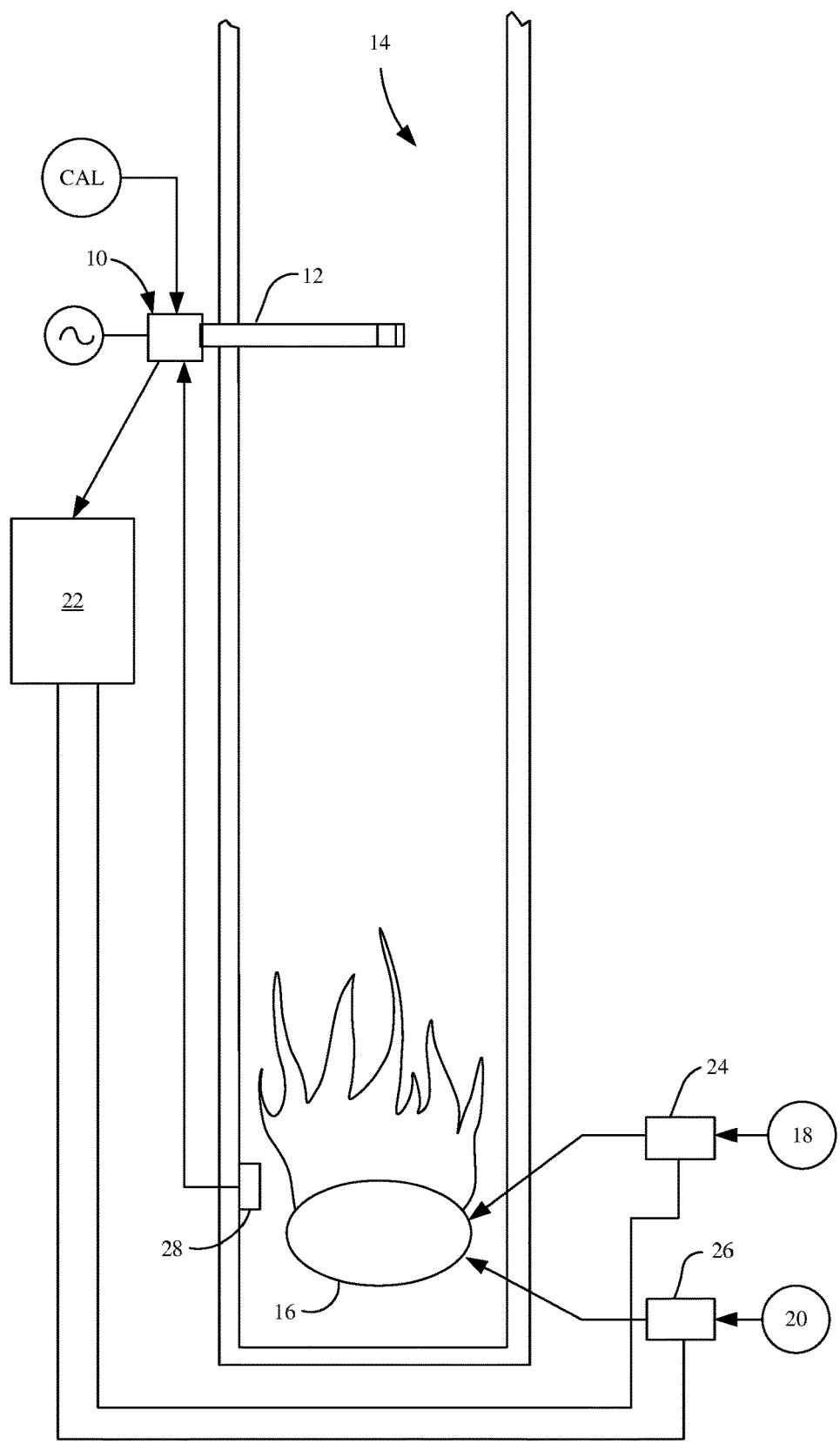
FIG. 1 is a diagrammatic view of an in-situ process oxygen analyzer transmitter installation with which embodiments of the present invention are particularly applicable.

FIG. 1 is a diagrammatic view of an in-situ process oxygen analyzer transmitter installation with which embodiments of the present invention are particularly applicable. Transmitter 10 can be, for example, a Model 6888 Oxygen Transmitter available from Rosemount Inc., (an Emerson Automation Solutions company). Transmitter 10, in one example, includes probe assembly 12 that is substantially disposed within stack or flue 14 and measures oxygen content of the flue gas related to combustion occurring at burner 16. In one example, burner 16 is operably coupled to a source of air or oxygen source 18 and a source of combustion fuel. Each of sources 18 and 20 are controllably coupled to burner 16 in order to control the combustion process. Transmitter 10 measures the amount of oxygen in the combustion exhaust flow and provides an indication of the oxygen level to combustion controller 22. Controller 22 controls one or both of valves 24 and 26 to provide closed loop combustion control. Controller 22 may operate automatically such that an indication of too much or too little oxygen in the exhaust flow results in a change in the amount of oxygen or fuel provided to burner 16.

Figure 2:
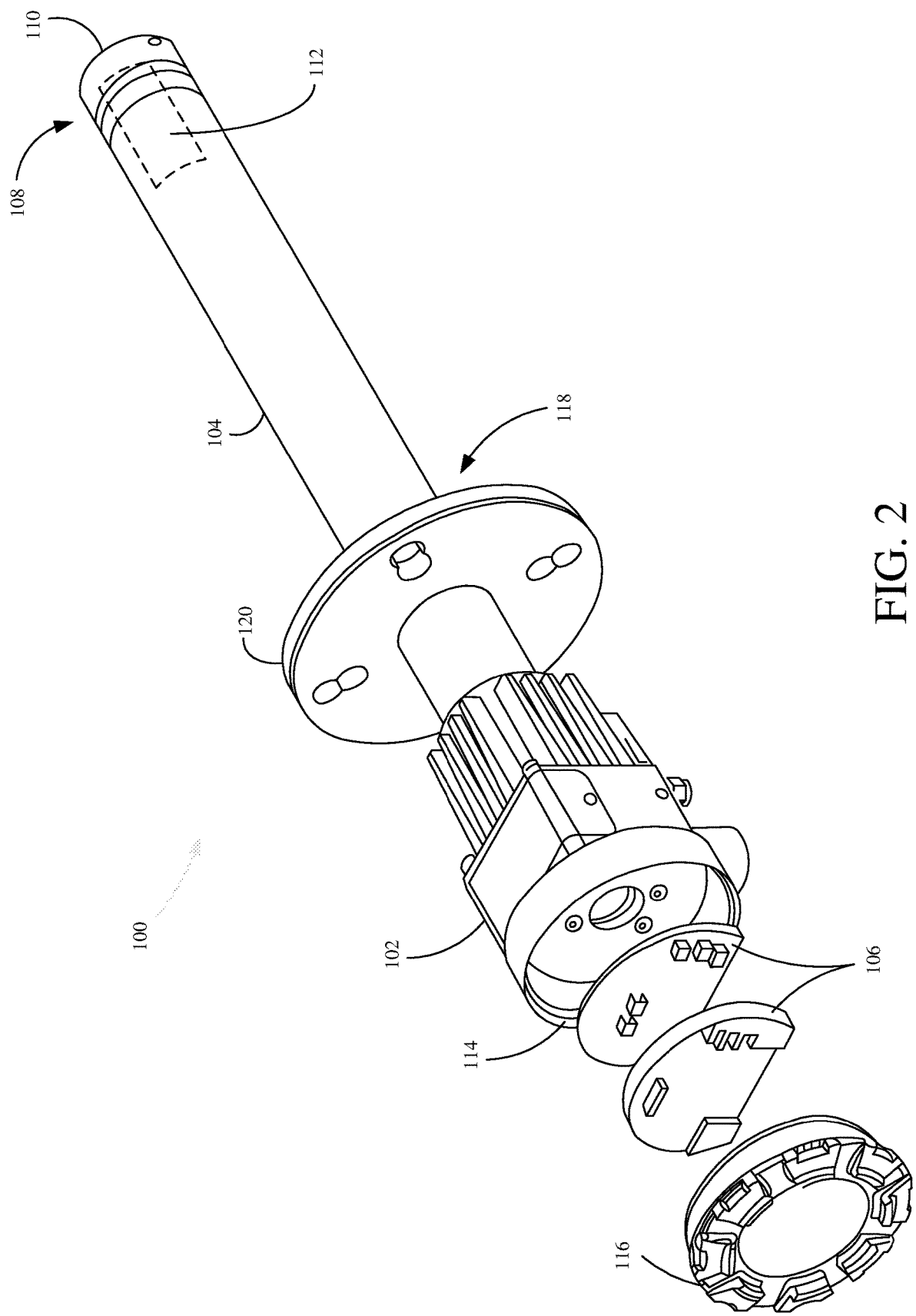
FIG. 2 is a diagrammatic perspective view of a combustion oxygen transmitter with which embodiments of the present invention are particularly applicable.

FIG. 2 is a diagrammatic perspective view of a combustion oxygen transmitter with which embodiments of the present invention are particularly applicable. Transmitter 100 includes housing 102, probe body 104, and electronics 106 with a protective cover 116. Probe body 104 has a distal end 108 where flame arrester 110 is mounted. Flame arrester 110 is configured to allow hot gases to flow through to the oxygen cell 112, illustrated in phantom in FIG. 2. These gases are hot enough to become explosive or otherwise generate ignition, so an important function of flame arrester 110 is to draw heat from the gases and the minimize the amount of oxygen around the gases to reduce the risk of explosion or ignition.

Housing 102 has a chamber 114 that is sized to house electronics 106. Additionally, housing 102 includes internal threads that are adapted to receive and mate with external threads on cover 116 in order to generate a hermetic seal. Additionally, housing 102 includes a bore or aperture therethrough allowing electrical interconnection between electronics 106 and measuring cell 112 disposed within distal end 108 of probe 104.

Probe body 104 is configured to extend within a flue, such as flue 14. Probe body 104 includes a proximal end 118 that is adjacent to flange 120. Flange 120 is used to mount or otherwise secure transmitter 100 to the sidewall of a duct. When so mounted, transmitter 100 may be completely supported by the coupling of flange 120 to the duct wall.

Electronics 106 may provide heater control and signal conditioning. Further, electronics 106 may provide a linear 4-20 mA signal representing flue gas oxygen concentration. In one example, electronics 106 is a microprocessor that is able to execute programmatic steps to provide the functions of flue gas oxygen measurement and communication. However, in some examples, transmitter 100 may simply be a "direct replacement" probe with no electronics and thus sending raw millivolt signals for the sensing cell and thermocouple providing indications representative of the oxygen concentration and cell, respectively.

Figure 3A:
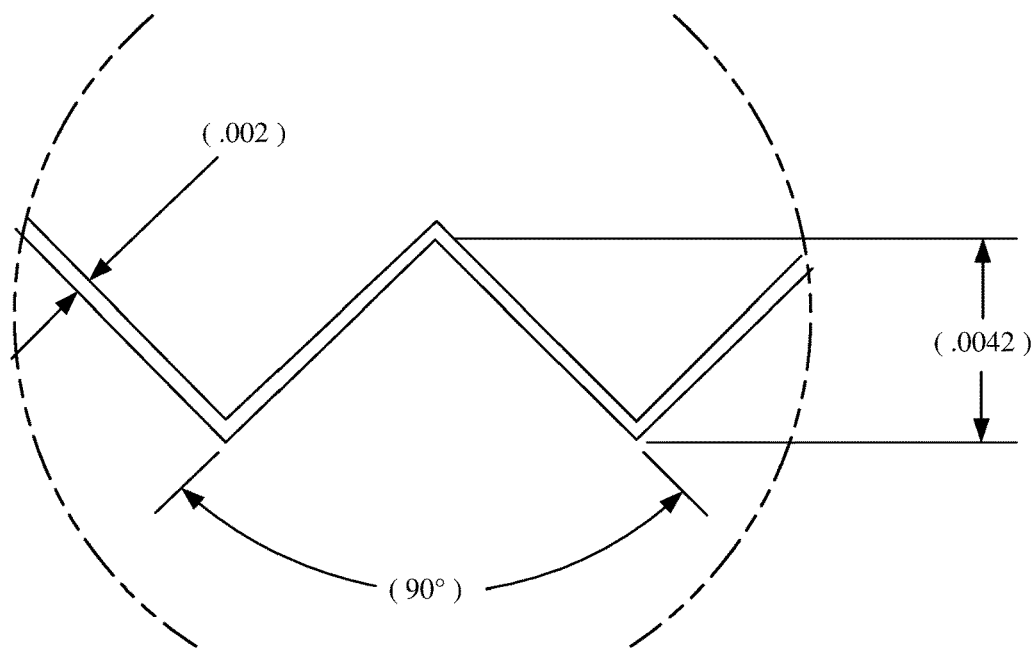
FIGS. 3A and 3B are diagrammatic views of a known flame arrester design.
Figure 3B:
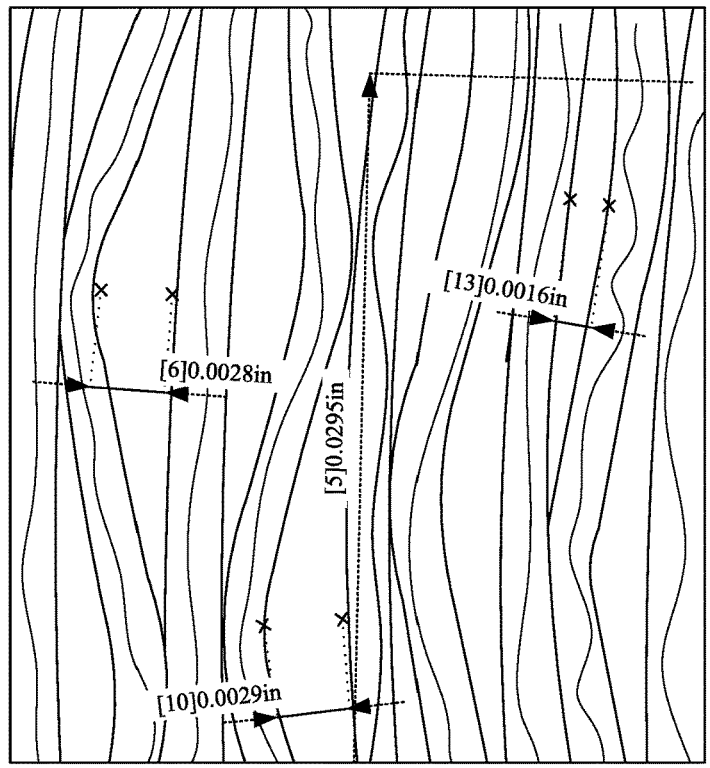

FIGS. 3A and 3B are diagrammatic views of a known flame arrester design. Such designs typically use a thin sheet metal part, such as that illustrated in FIG. 3A. The thin sheet metal is formed to have a ripple with peaks and valleys as shown. In the illustrated example, the thickness of the sheet metal is approximately 0.002 inches thick, and the ripple that is formed has approximately 90° angles with the distance between peaks and valleys being approximately 0.0042 inches. FIG. 3B is an enlarged diagrammatic view showing the formed ripple from FIG. 3A becoming deformed or flattened when the sheet metal part is rolled into a final coiled form. This deformation changes the flow values of the design in a way that can vary with manufacturing techniques. Accordingly, there can be undesirable variability when using flame arresters manufactured in accordance with prior techniques.

In accordance with one embodiment described herein, an improved flame arrester is provided, that employs two helixes with their respective axes separated, preferably by approximately 90°. This pair of cross helixes generates a mesh form which is easily adjustable at the design stage (for example specifying wall thickness and pitch) in order to achieve different flow rates. Moreover, the performance of the flame arrester response time generally depends on the amount of flow that is allowed to pass through the apparatus.

Figure 4:
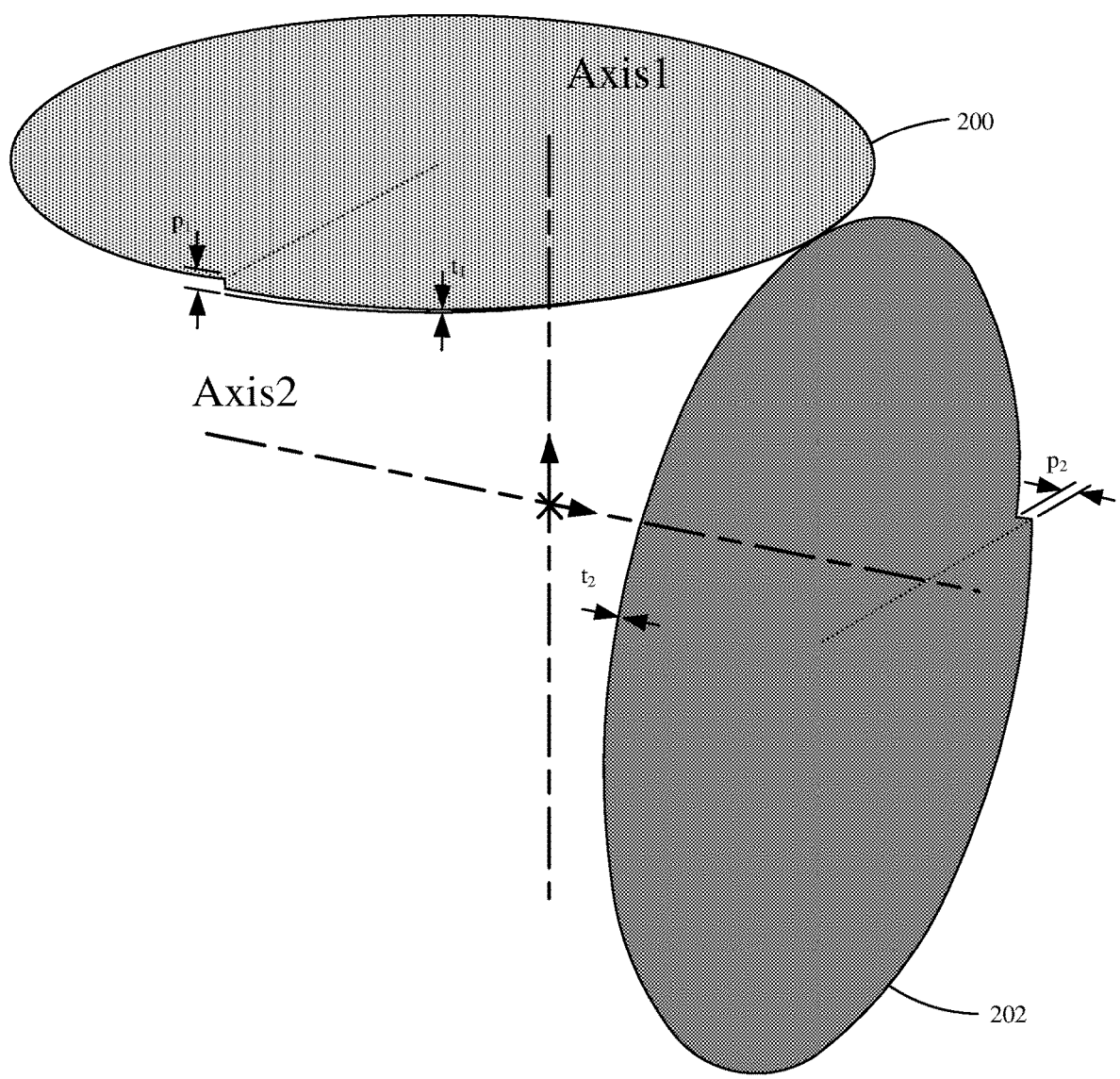
FIG. 4 is a diagrammatic view of a pair of orthogonal axes (axis 1, axis 2) with a respective helical section or 360° step of each of the pair of cross helixes.

FIG. 4 is a diagrammatic view of a pair of orthogonal axes (Axis 1, Axis 2) with a respective step or singular 360° iteration of each of the pair of cross helixes. As can be seen in FIG. 4, first helix step 200 has a central axis that is generally aligned with Axis 1 and has wall thickness $t_1$ and pitch $p_1$. Similarly, helix step 202 has a central axis that is aligned with Axis 2 and has thickness $t_2$ and pitch $p_2$. Each respective helix is generated by basically iterating the individual helical sections as they step along in the axial direction.

Figure 5:
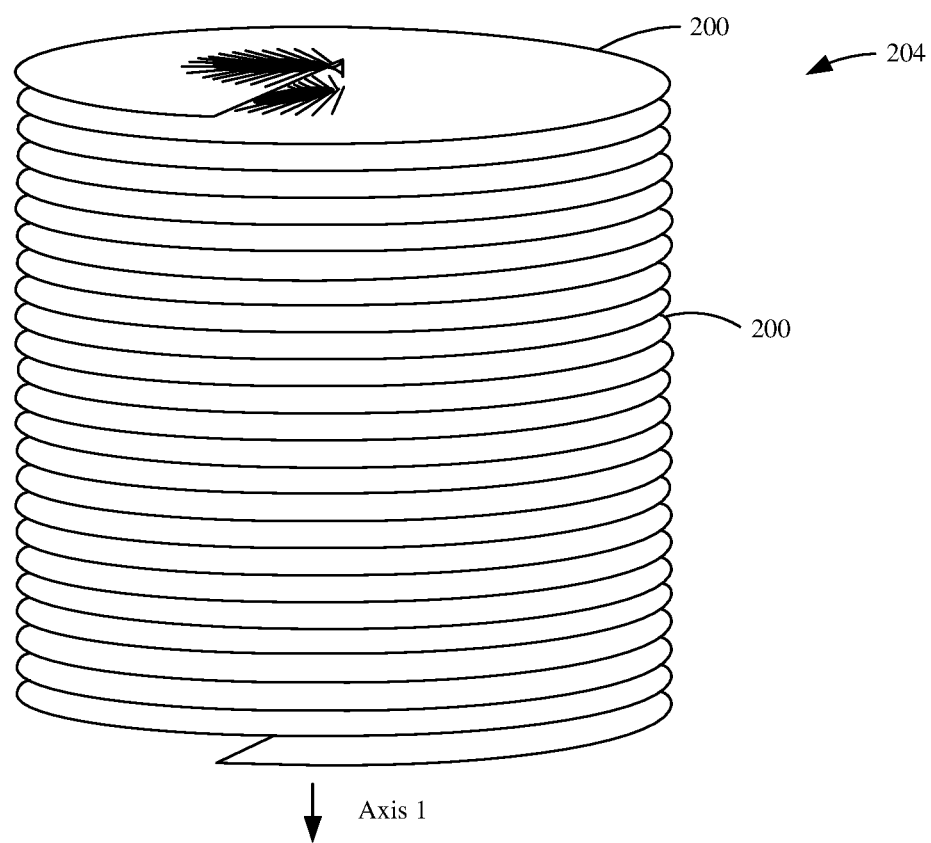
FIG. 5 is a diagrammatic view illustrating an entire helix formed of a continuous helix over a desired length.

FIG. 5 is a diagrammatic view illustrating an entire helix 204 patterned over a desired length to form a continuous helical part.

Figure 6A:
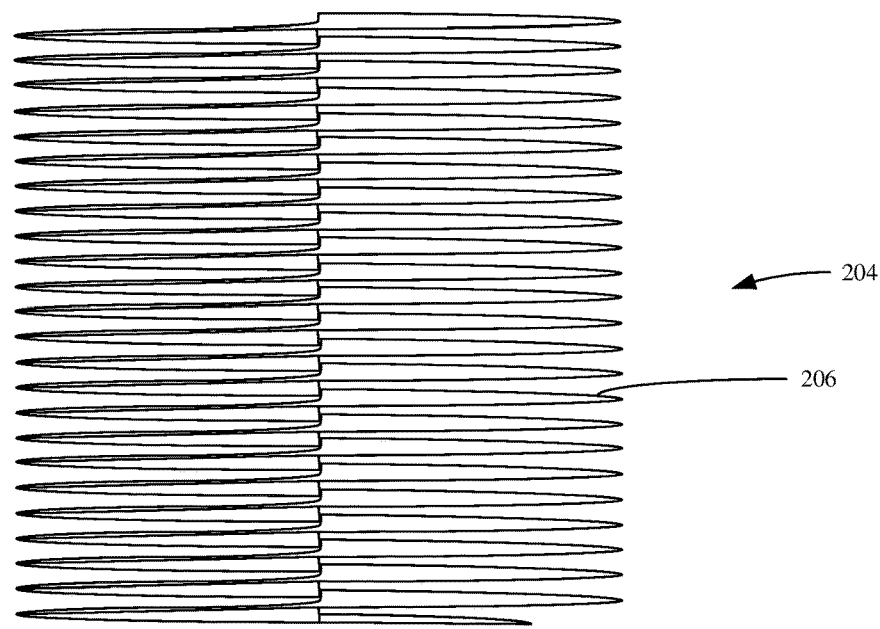
FIG. 6A is a diagrammatic side elevation view of the helix shown in perspective in FIG. 5.

FIG. 6A is a diagrammatic side elevation view of helix 204 shown in perspective in FIG. 5. As can be seen, a number of spaces or channels 206 exist between the helical sidewalls of helix 206.

Figure 6B:
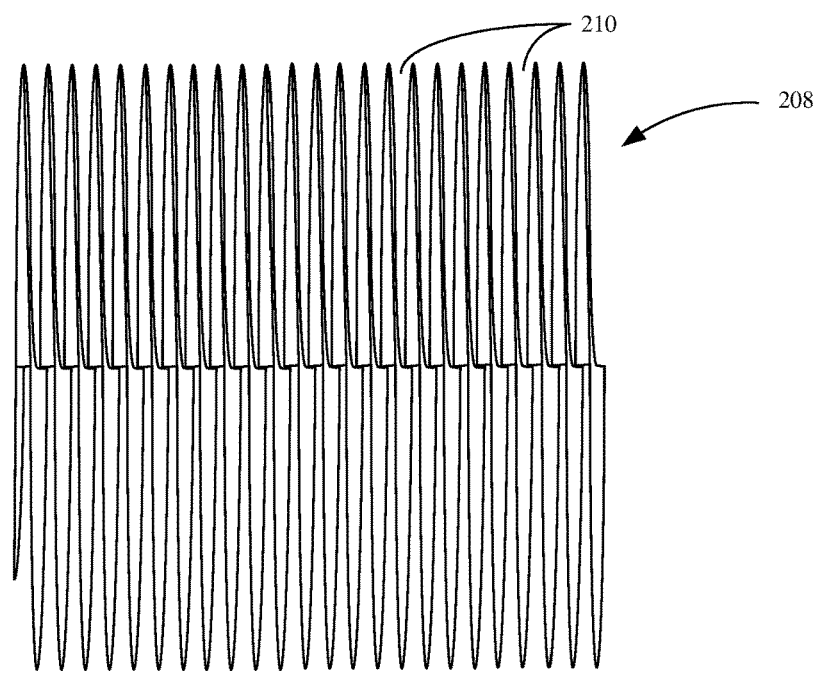
FIG. 6B is a side elevation view of a continuous helix formed over a desired length aligned with an axis orthogonal to the axis shown in FIG. 6A.

FIG. 6B is a side elevation view of helix 208 formed by a number of helical sections 202 aligned with axis 2. As can be seen, helix 208 also includes a number of spaces or channels 210 between the sidewall of helix 208.

Figure 7:
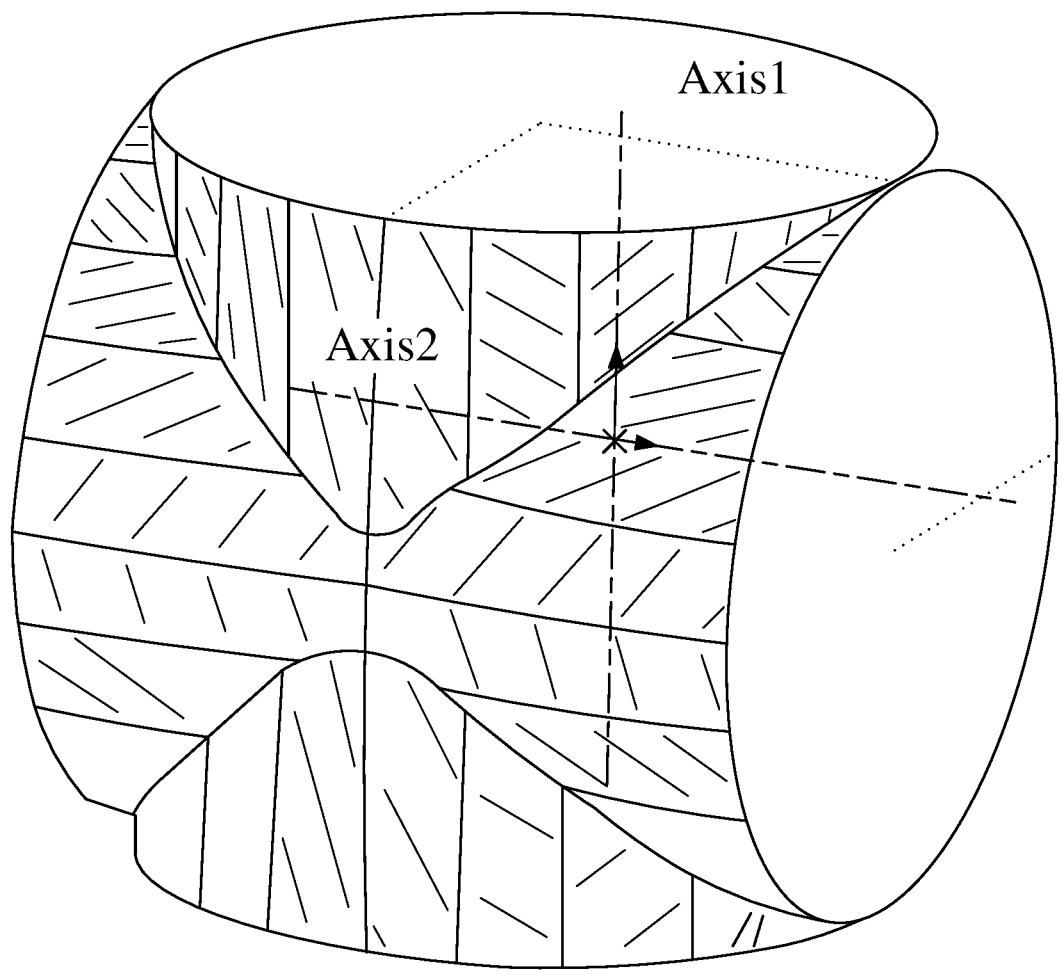
FIG. 7 is a diagrammatic view of a form generated by the superposition of the pair of cross helixes in accordance with an embodiment of the present invention.

FIG. 7 is a diagrammatic view of a form generated by the superposition of the pair of cross helixes in accordance with an embodiment of the present invention. In the design and modeling stage, helix 204 and 208 with their preferably orthogonal axes are superimposed over one another to generate a cross helical form shown in FIG. 7. The manufacture or the superimposed cross helical form is generally not viable with traditional flame arrester manufacturing techniques. Accordingly, embodiments described herein are generally manufactured using additive machining or EDM manufacturing. Such techniques provide the ability to easily adjust the design and provide confidence that the final part is produced in a way in which the design is intended. Moreover, the design is easily scaled in the development stage to increase or decrease various dimensions in order to provide suitable forms which can then be manufactured using additive techniques or EDM manufacturing. For example, the helix can be adjusted by changing the pitch dimension either making it tighter or more loose depending on test results. Once the form illustrated in FIG. 7 is manufactured, the overall structure is then cut to the desired shape.

Figure 8:
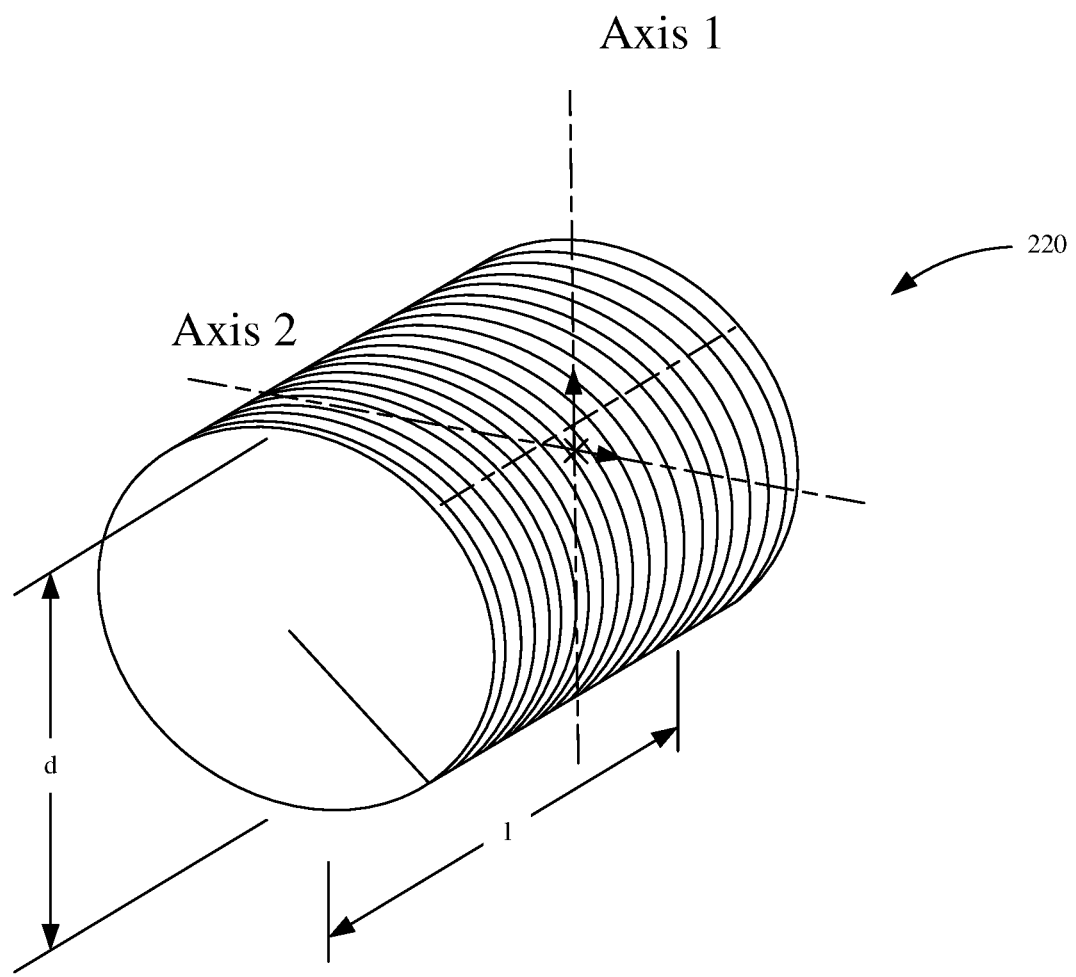
FIG. 8 is a diagrammatic view of a cross helical flame arrester element cut to a desired shape in accordance with one embodiment.

FIG. 8 is a diagrammatic view of a cross helical flame arrester element cut to a desired shape in accordance with one embodiment. As can be seen, the overall structure has been cut to a cylindrical shape having length 1 and diameter d. This cut-to-shape element 220 can then be inserted into a suitable housing, such as threaded housing 222. However, the desired shape and size of the flame arrester element can also be combined with the housing in the design process stage and manufactured as a single piece.

Figure 9:
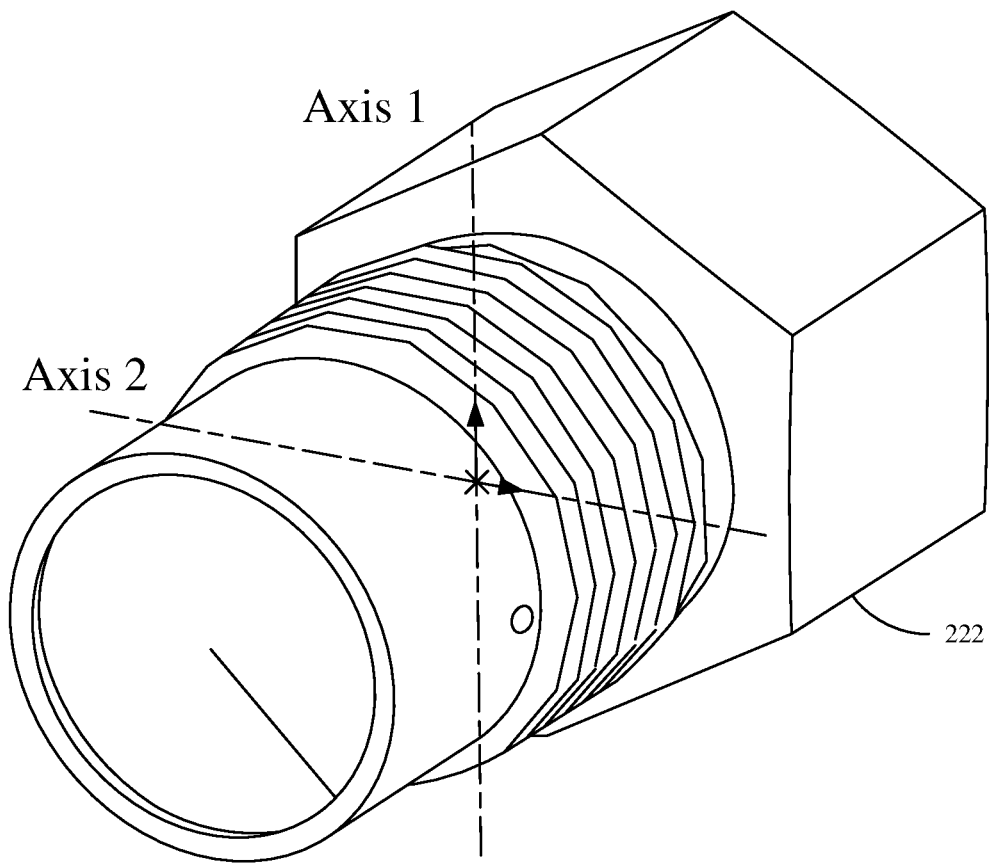
FIG. 9 is a diagrammatic view of a cross helical flame arrester element cut to shape and inserted into a threaded housing in accordance with an embodiment of the present invention.

FIG. 9 is a diagrammatic view of a cross helical flame arrester element cut to shape and inserted into a threaded housing in accordance with an embodiment of the present invention. shown in FIG. 9. The completed mesh end of the threaded housing can then simply be threaded to the end of a combustion probe or other suitable process device in order to provide the flame arresting function. The material used for the flame arrester can vary based upon temperature and exposure to particular substances. However, it is generally preferred that the material used for the additive printing of the flame arrester element be a metal or composite that is amenable to additive manufacturing techniques, such as 3D printing. Examples of suitable materials include, without limitation, stainless steel, cobalt chrome, maraging steel, aluminum, nickel alloy, and titanium.

Figure 10:
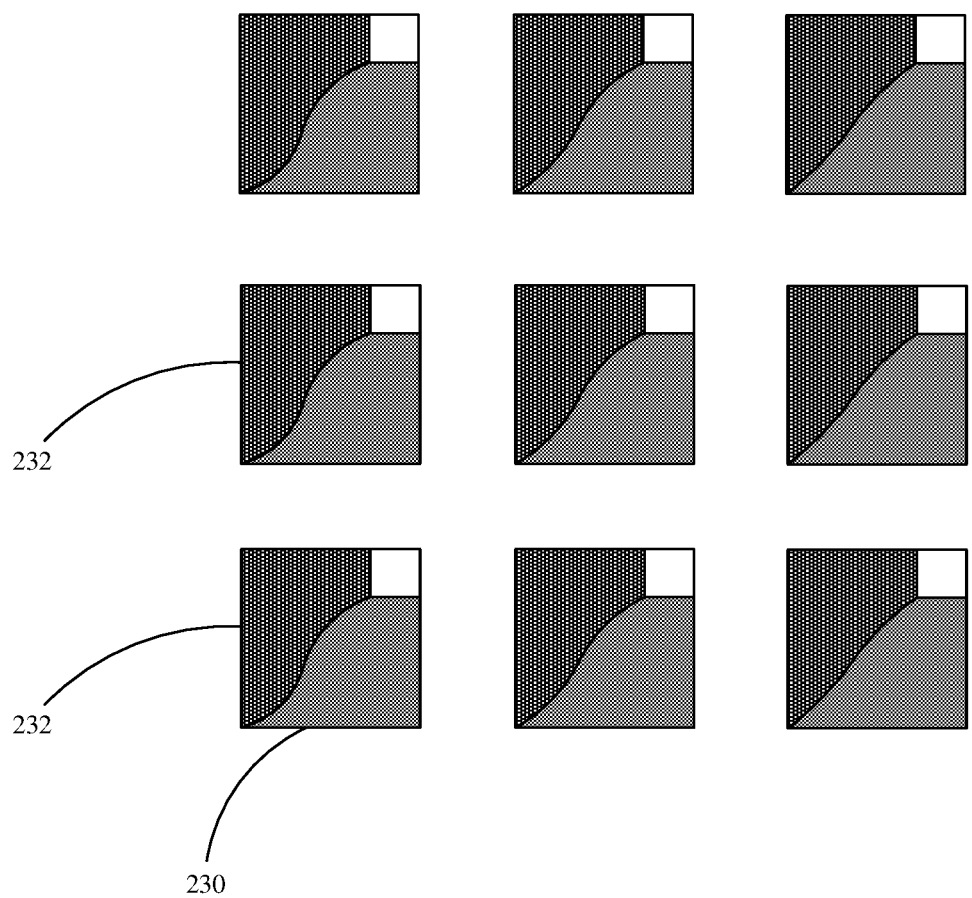
FIG. 10 is an enlarged view of an end of a cross helical flame arrester in accordance with one embodiment.

FIG. 10 is an enlarged view of an end of a cross helical flame arrester in accordance with one embodiment. As can be seen, the end 230 generally has a grid shape with a number of apertures 232 extending from end 230 in a path defined by the superimposed helixes. In the example shown in FIG. 10, these paths extend into the plane of the page and upwardly to the right.

Figure 11:
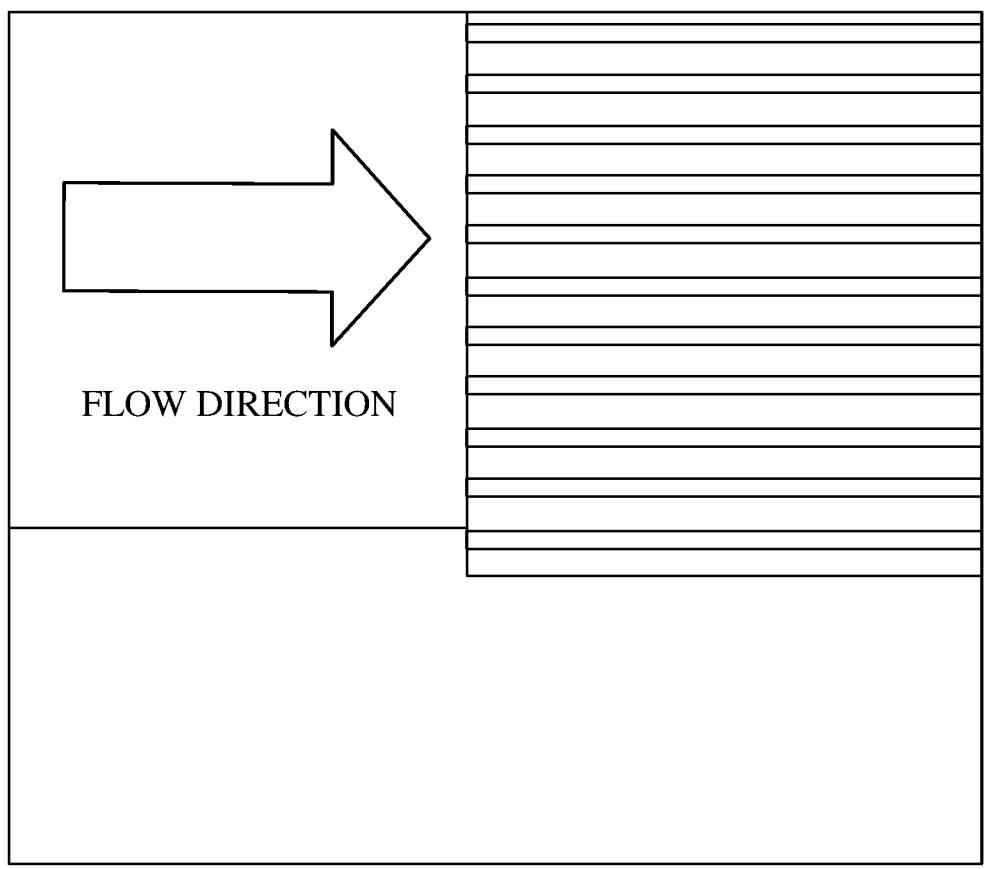
FIG. 11 is a diagrammatic view of a slice of the mesh illustrating the flow direction of gases through the flamer arrester.

FIG. 11 is a diagrammatic view of a slice of the mesh illustrating the flow direction of gases through the flamer arrester. As can be seen, flow direction 234 passes through a number of channels 236 to the oxygen measuring cell. The flow path has a slight helical angle (not shown in FIG. 11) so that it is not a straight path which helps heat be drawn from the hot air/gases.

Figure 12:
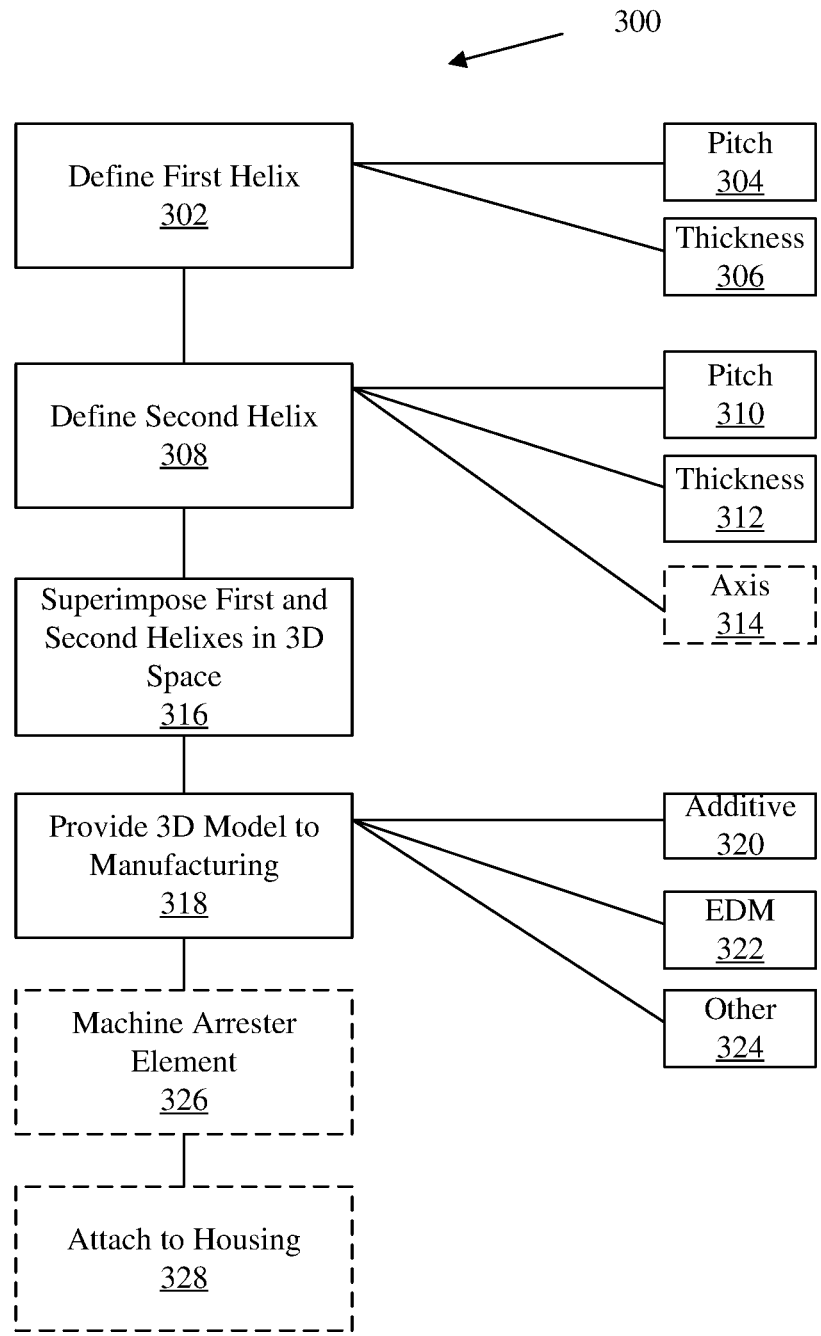
FIG. 12 is a flow diagram of a method of manufacturing a cross-helix flame arrester in accordance with an embodiment of the present invention.

FIG. 12 is a flow diagram of a method of manufacturing a cross-helix flame arrester in accordance with an embodiment of the present invention. Method 300 begins at block 302 where the first helix is defined. The definition of the first helix generally includes specification of the pitch 304 and the wall thickness. Next, at block 308, the second helix is defined. Again, specification of the second helix also generally includes defining the pitch 310 and the wall thickness 312. Additionally, the second helix can have its axis defined relative to the first helix, as indicated at block 314. Preferably, the axis of the second helix is 90 degrees from the first helix such that they are orthogonal. However, embodiments can be practiced where other spacing can be used as long as the first and second axis are not parallel. Once the first and second helixes are defined, method 300 proceeds to block 316 where the first and second helixes are superimposed. In one embodiment, this means that the first and second axes are positioned to intersect. However, embodiments can be practiced that allow for some spacing between the first and second axes. With the first and second helixes superimposed, a three-dimensional shape or model is defined. This model is then provided to a suitable manufacturing device or facility, as indicated at block 318, in order to generate a physical object based on the three-dimensional model. Suitable manufacturing devices or facilities includes additive manufacturing, such as 3D printing, as indicated at reference numeral 320, EDM 322, or other suitable techniques, as indicated at reference numeral 324.

Additive manufacturing generally refers to technologies or techniques that generate three dimensional objects one layer (which is generally very thin) at a time. Each deposited layer fuses or bonds to the layer below it. This is because the materials used are often heated to temperatures at or near their melting point. It is also possible, in additive manufacturing to have different substances for layering material. Additive manufacturing can provide very intricate internal details that simply could not be generated with traditional machining. In additive manufacturing, the objects are generally defined as a 3D model by using CAD or some other suitable software. These models are often saved as .stl files that can be digitally sliced into the very fine layers, the additive manufacturing device then deposits or otherwise generates material on a printing surface. Once a given layer is complete, the printing head indexes up one layer thickness and begins depositing the next layer upon the previous layer.

EDM, as used herein, refers to electrical discharge machining. EDM is generally machining method that is mainly used for hard metals that would be difficult to machine with traditional techniques. EDM typically generally works with electrically conductive materials. In EDM, material is removed from a workpiece using a number of current discharges or sparks between two electrodes. EDM can be used to generate intricate contours or cavities in metals.

Method 300 continues at optional block 326, illustrated in phantom. Once the arrester element is generated at block 318, it may require further machining before being suitable for being attached to its housing. Thus, additional machining to the element, such as turning it to a specified diameter or cutting it to length, can be provided at block 326. Once the optional additional machining is complete, the flame arrester element is mounted to a housing, such as that shown in FIG. 9. The element can be attached to the housing using any suitable techniques, such as welding, brazing, clamping, or using a press-fit. The finished flame arrester may then be simply threaded into a distal end of a probe body or other suitable process device.

Although the present invention has been described with reference to preferred embodiments, workers skilled in the art will recognize that changes may be made in form and detail without departing from the spirit and scope of the invention. For example, while embodiments described herein are described with respect to a process combustion analyzer, it is expressly contemplated that embodiments are suitable for any process device for which flame arrest is required or beneficial.

What is claimed is:

1. A flame arrester for a process device, the flame arrester comprising:
   a flame arrester element formed of a first helix having a first longitudinal axis and a second helix having a second longitudinal axis, wherein the first longitudinal axis and the second longitudinal axis are unparallel;
   a housing configured to mount to the process device, the housing having the flame arrester element attached thereto.

2. The flame arrester of claim 1, wherein the first longitudinal axis and the second longitudinal axis are orthogonal.

3. The flame arrester of claim 1, wherein the first longitudinal axis and the second longitudinal axis intersect.

4. The flame arrester of claim 1, wherein the flame arrester element is formed by additive manufacturing.

5. The flame arrester of claim 1, wherein the flame arrester element is formed by electrical discharge machining (EDM).

6. The flame arrester of claim 1, wherein the flame arrester element is formed of a metal.

7. The flame arrester of claim 6, wherein the metal is selected form the group consisting of stainless steel, cobalt chrome, maraging steel, aluminum, nickel alloy, and titanium.

8. The flame arrester of claim 1, wherein an end of the flame arrester element has a grid shape with a number of apertures.

9. A combustion analyzer comprising:
   a probe body having an oxygen sensing cell disposed therein, the probe body having a distal end with a flame arrester attached thereto, the flame arrester being configured to be interposed between a process gas and the oxygen sensing cell, the flame arrester having a flame arrester element formed by a pair of cross-helixes, each of the pair of cross-helixes having a longitudinal axis that is unparallel to a longitudinal axis of the other; and
   a housing coupled to the probe body and having electronics therein, the electronics being coupled to the oxygen sensing cell and configured to generate an oxygen output indicative oxygen concentration in the process gas.

10. The combustion analyzer of claim 9, wherein the flame arrester element is formed using additive manufacturing.

11. The combustion analyzer of claim 10, wherein the flame arrester element is formed of metal.

12. The combustion analyzer of claim 9, wherein the flame arrester is threadably coupled to the distal end of the probe body.

13. The combustion analyzer of claim 9, wherein the flame arrester element is attached to a threaded flame arrester housing that is threadably coupled to the distal end of the probe body.

14. The combustion analyzer of claim 9, wherein the cross-helixes are orthogonal to one another.

15. The combustion analyzer of claim 9. wherein each longitudinal axes of the pair of helixes intersect one another.

16. The combustion analyzer of claim 9, wherein an end of the flame arrester has a grid shape.

* * * * *